United States Patent
Michler et al.

(10) Patent No.: US 12,128,192 B2
(45) Date of Patent: Oct. 29, 2024

(54) HEART VENT CATHETER AND METHOD OF USE

(71) Applicants: Robert E. Michler, New York, NY (US); Albert N. Santilli, Pepper Pike, OH (US)

(72) Inventors: Robert E. Michler, New York, NY (US); Albert N. Santilli, Pepper Pike, OH (US)

( * ) Notice: Subject to any disclaimer, the term of this patent is extended or adjusted under 35 U.S.C. 154(b) by 989 days.

(21) Appl. No.: 17/120,954

(22) Filed: Dec. 14, 2020

(65) Prior Publication Data

US 2021/0162165 A1   Jun. 3, 2021

Related U.S. Application Data

(63) Continuation-in-part of application No. 15/729,035, filed on Oct. 10, 2017, now abandoned, which is a
(Continued)

(51) Int. Cl.
*A61M 25/00* (2006.01)
*A61M 25/09* (2006.01)
(Continued)

(52) U.S. Cl.
CPC ...... *A61M 25/007* (2013.01); *A61M 25/0043* (2013.01); *A61M 25/09041* (2013.01);
(Continued)

(58) Field of Classification Search
CPC ............. A61M 25/10; A61M 25/104; A61M 2025/1052; A61M 2025/1095; A61M 2025/1097
See application file for complete search history.

(56) References Cited

U.S. PATENT DOCUMENTS

| | | |
|---|---|---|
| 5,147,315 A | 9/1992 | Weber |
| 5,292,309 A | 3/1994 | Van Tassel |

(Continued)

OTHER PUBLICATIONS

DLP left heart vent catheters, Medtronic, Inc., Minneapolis, Minn.: http://www.medtronic.com/mics/documents/200805572_EN.pdf (p. VII-5).

(Continued)

*Primary Examiner* — Todd J Scherbel
(74) *Attorney, Agent, or Firm* — Wayne D. Porter, Jr.

(57) ABSTRACT

A heart vent catheter includes an elongate, flexible tube that defines a first passageway. The catheter has a distal end, a central portion, and a proximal end. A balloon is included as part of the distal end and surrounds at least a portion of the tube. A plurality of first openings are formed in the tube adjacent the balloon on the forwardmost side of the balloon. A plurality of second openings can be formed in the tube adjacent the balloon on the proximal side of the balloon. After the distal end has been inserted into a desired part of a patient's heart, such as the left ventricle, the balloon can be inflated so as to engage a part of the heart such as the mitral valve and thereby prevent undesired withdrawal of the catheter. The proximal end includes a formation that can be connected to a vacuum source. The openings in the tube in the distal end permit blood, other fluid, debris and/or air to be withdrawn from the heart through the first passageway under suction. After the surgical procedure has been completed, the balloon can be collapsed and the catheter can be withdrawn from the heart.

4 Claims, 9 Drawing Sheets

Related U.S. Application Data continuation-in-part of application No. 15/591,325, filed on May 10, 2017, now abandoned, and a continuation-in-part of application No. 14/216,214, filed on Mar. 17, 2014, now abandoned, said application No. 15/591,325 is a continuation of application No. 14/216,214, filed on Mar. 17, 2014, now abandoned.

(60) Provisional application No. 61/801,957, filed on Mar. 15, 2013.

(51) Int. Cl.
  *A61M 25/10* (2013.01)
  *A61B 17/00* (2006.01)
  *A61M 25/01* (2006.01)

(52) U.S. Cl.
  CPC ... *A61M 25/10* (2013.01); *A61B 2017/00243* (2013.01); *A61M 25/0102* (2013.01); *A61M 25/0108* (2013.01); *A61M 2025/09133* (2013.01); *A61M 2025/1093* (2013.01); *A61M 2210/125* (2013.01)

(56) References Cited

U.S. PATENT DOCUMENTS

| | | | |
|---|---|---|---|
| 5,379,779 A | 1/1995 | Rowland | |
| 5,516,336 A | 5/1996 | Mcinnes | |
| 6,117,105 A * | 9/2000 | Bresnaham | A61M 25/1011 604/509 |
| 6,461,327 B1 * | 10/2002 | Addis | A61M 25/1011 604/509 |
| 6,673,039 B1 | 1/2004 | Bridges | |
| 6,726,651 B1 | 4/2004 | Robinson | |
| 6,821,265 B1 | 11/2004 | Bertolero | |
| 6,951,555 B1 * | 10/2005 | Suresh | A61M 25/0023 604/524 |
| 7,637,904 B2 | 12/2009 | Wingler | |
| 8,899,225 B2 | 12/2014 | Bosel | |
| 2002/0100482 A1 | 8/2002 | Sterman | |
| 2002/0165486 A1 * | 11/2002 | Bertolero | A61B 90/36 606/192 |
| 2003/0040736 A1 | 2/2003 | Stevens | |
| 2007/0049999 A1 | 3/2007 | Esch | |
| 2014/0058251 A1 | 2/2014 | Stigall | |
| 2014/0058257 A1 | 2/2014 | Stigall | |
| 2014/0303604 A1 * | 10/2014 | Michler | A61M 25/10 604/540 |

OTHER PUBLICATIONS

Left heart vent catheters, Medtronic, Inc., Minneapolis, Minn.: http://www.medtronic.com/content/dam/medtronic-com-m/mdt/cardio/documents/2011-medtrnc-cannulae-catalog.pdf (p. 77).

* cited by examiner

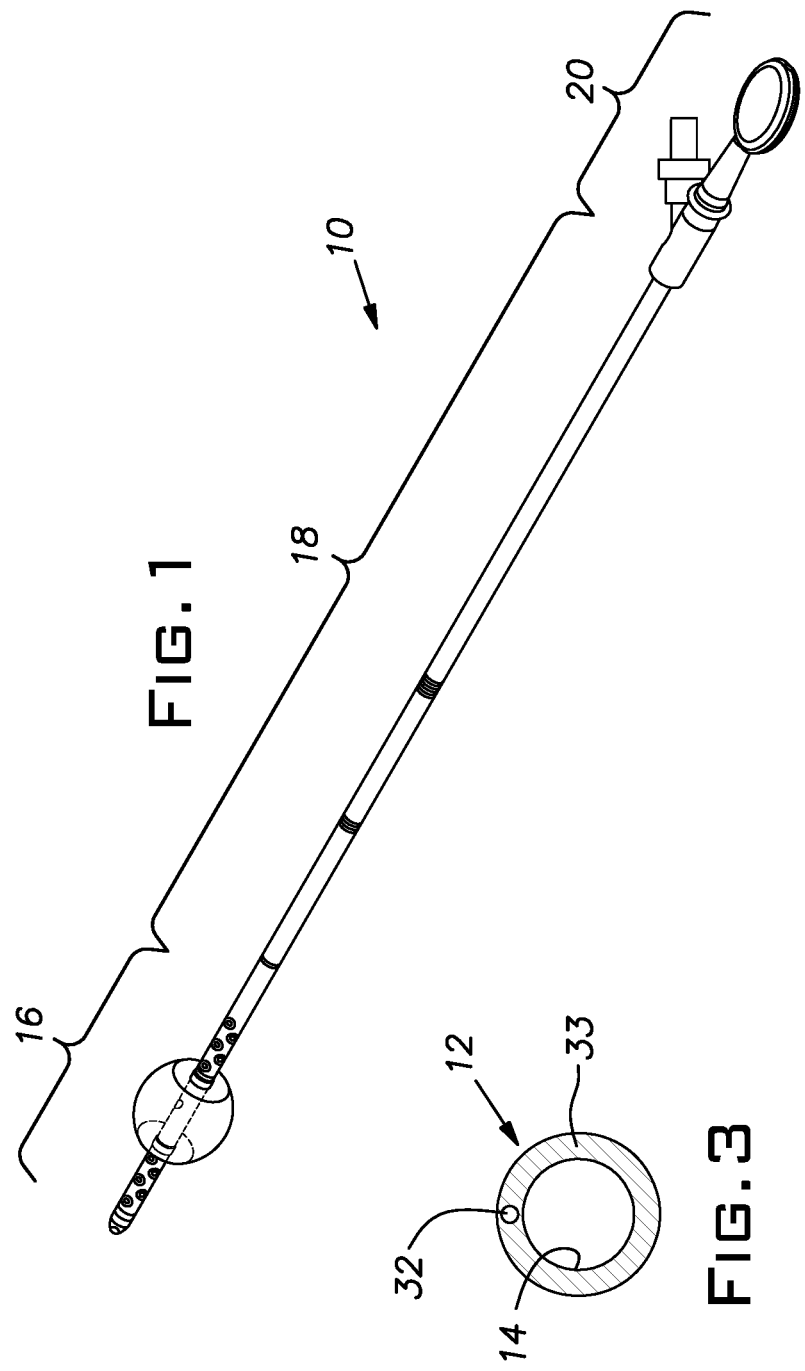
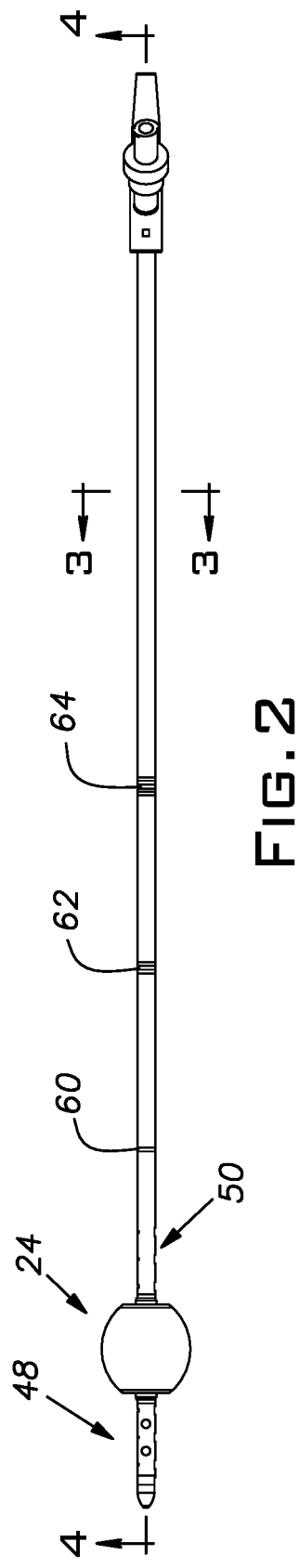

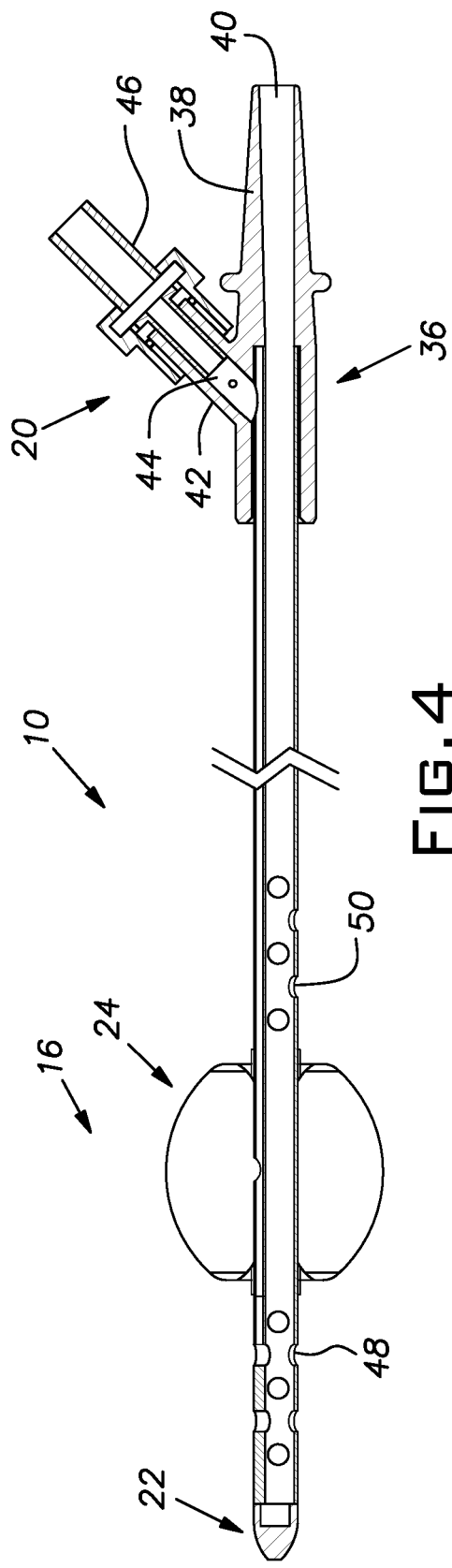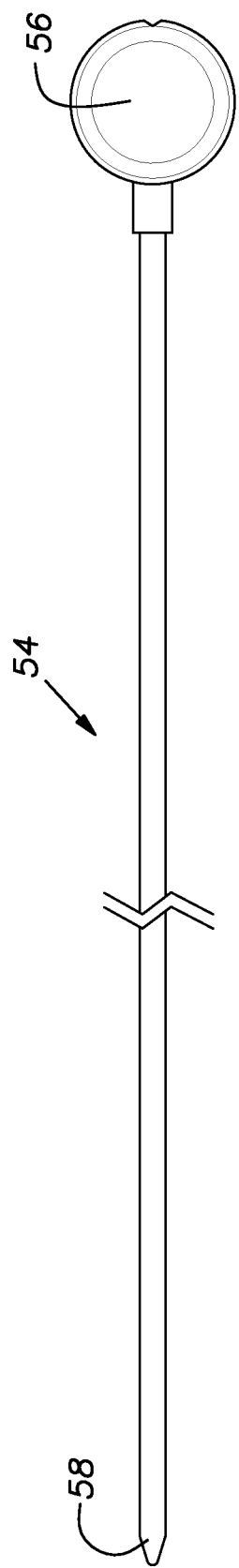
FIG. 4
FIG. 5

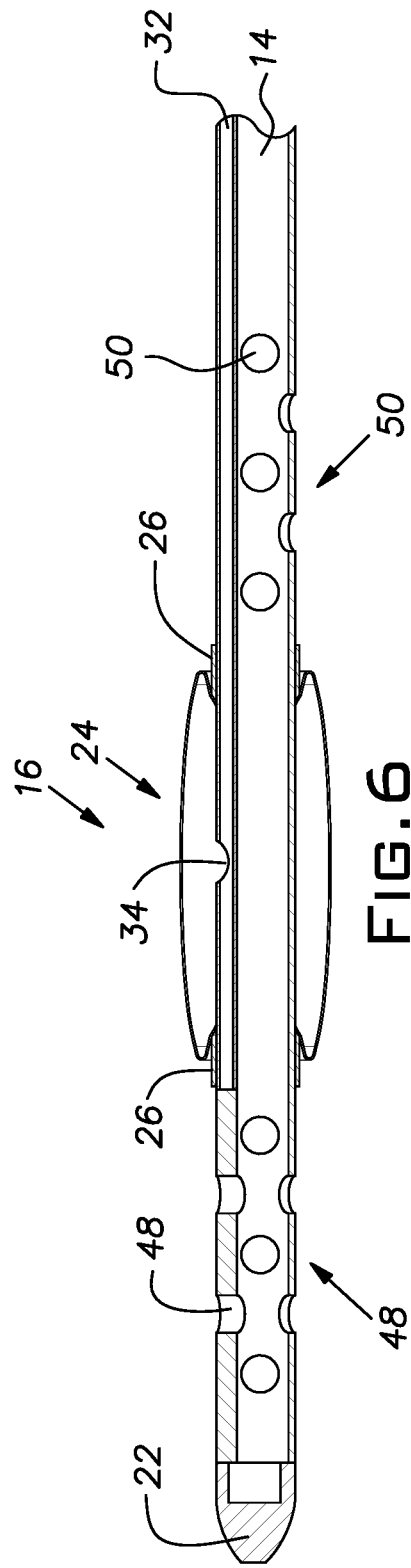
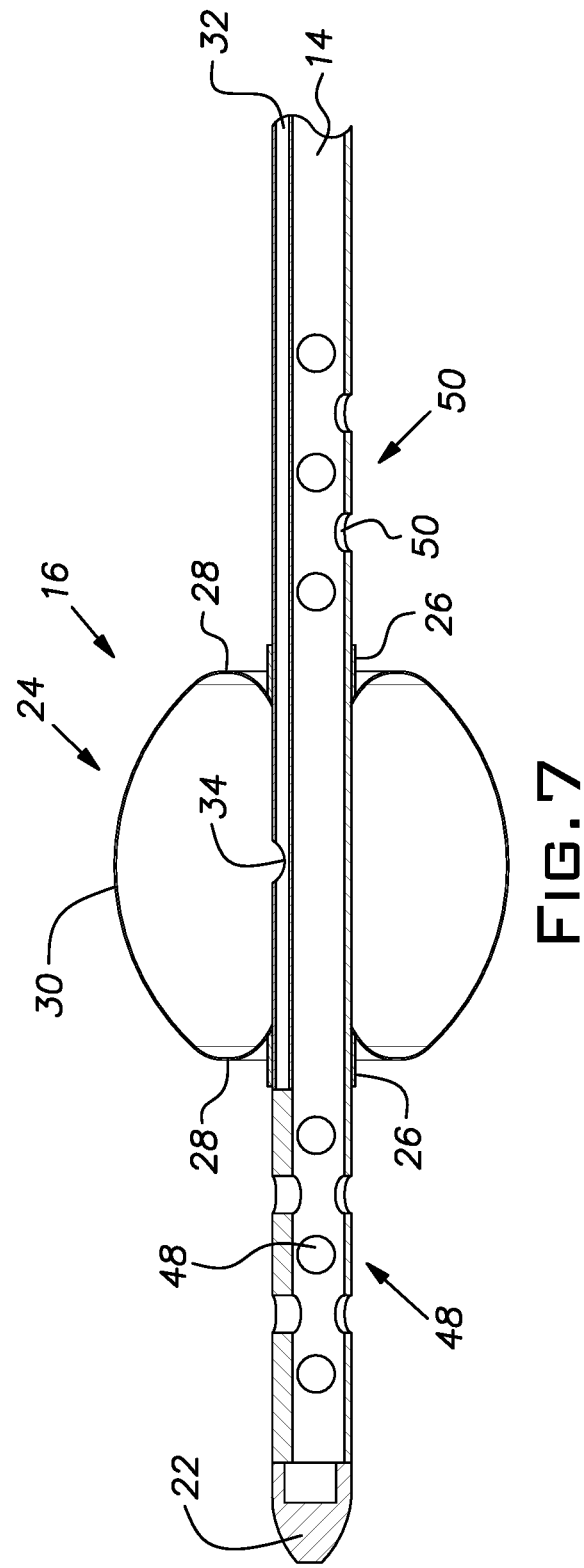

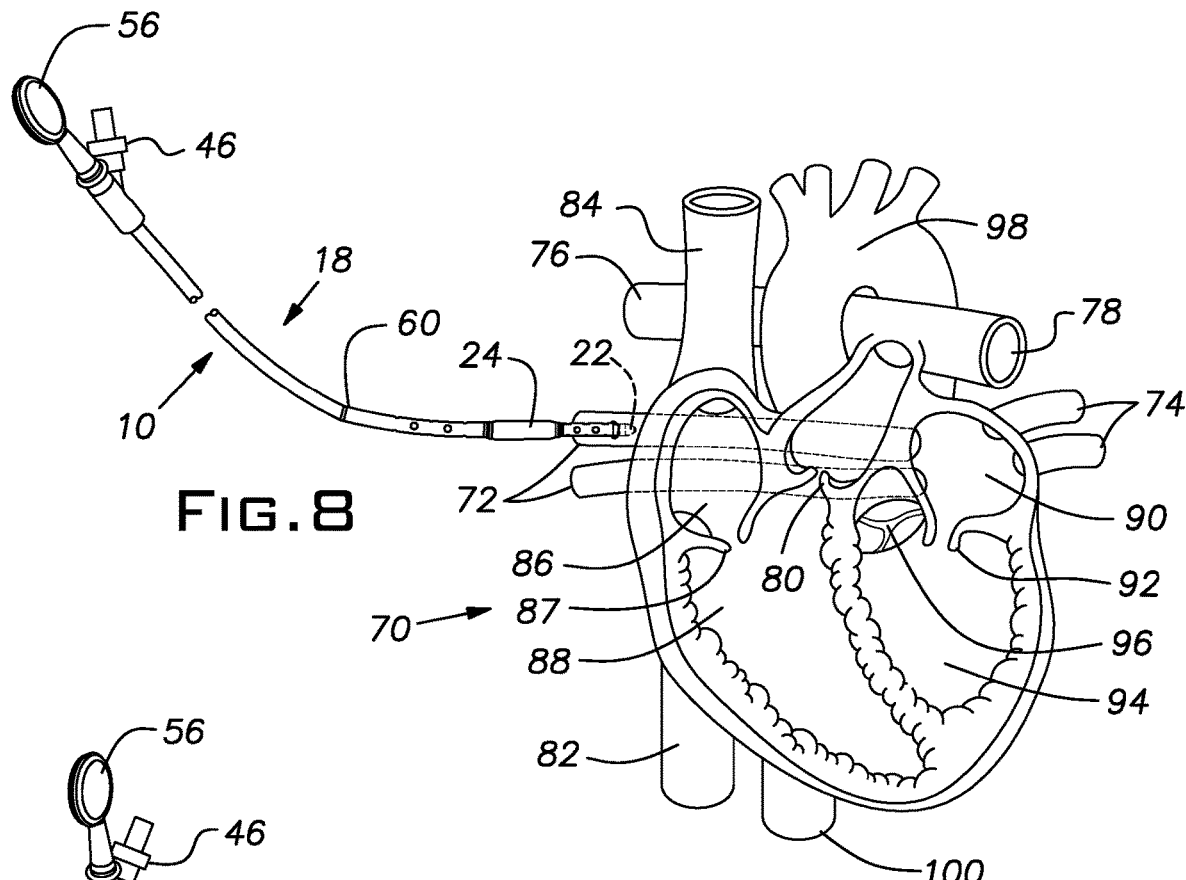
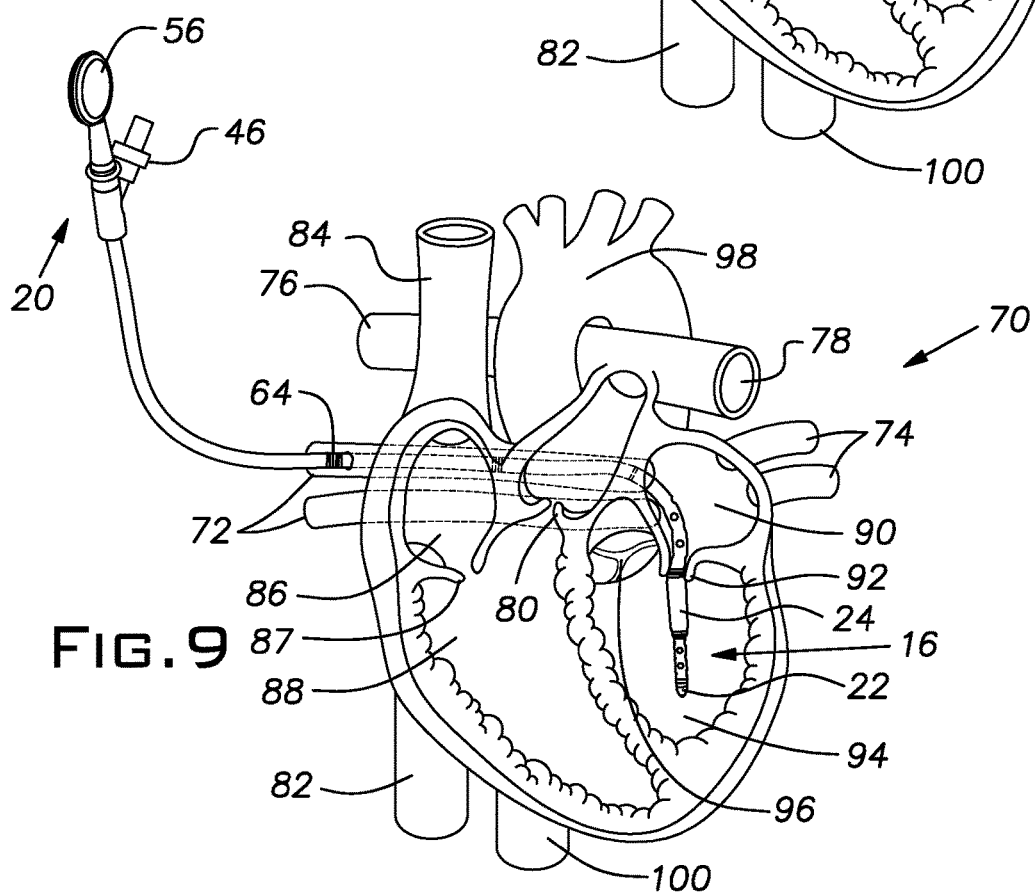

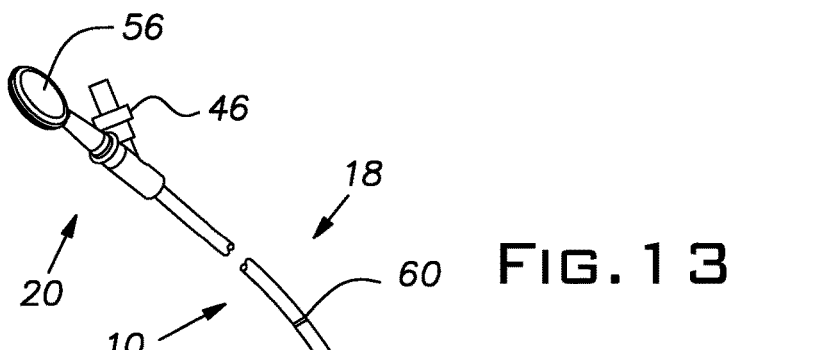
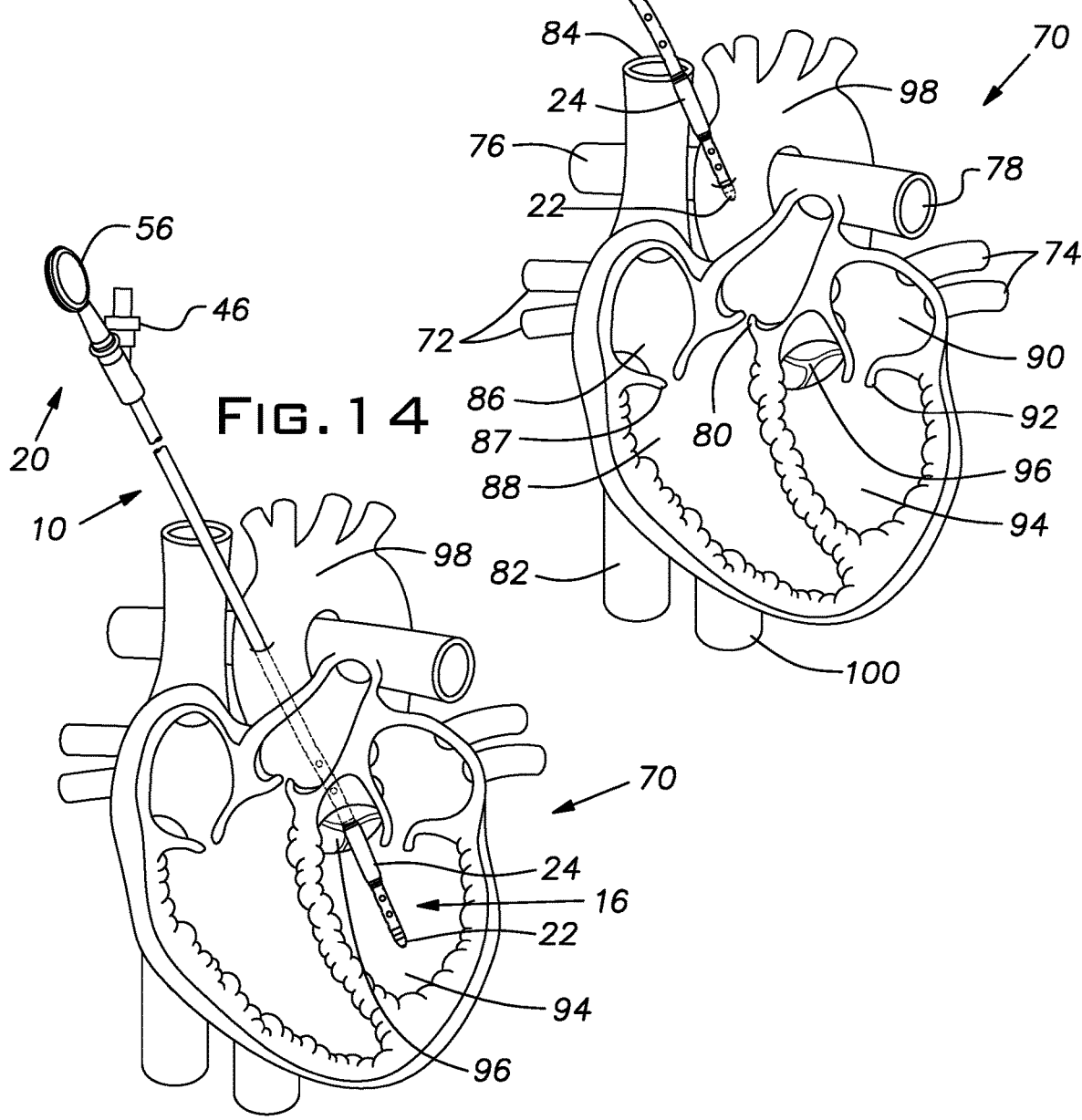

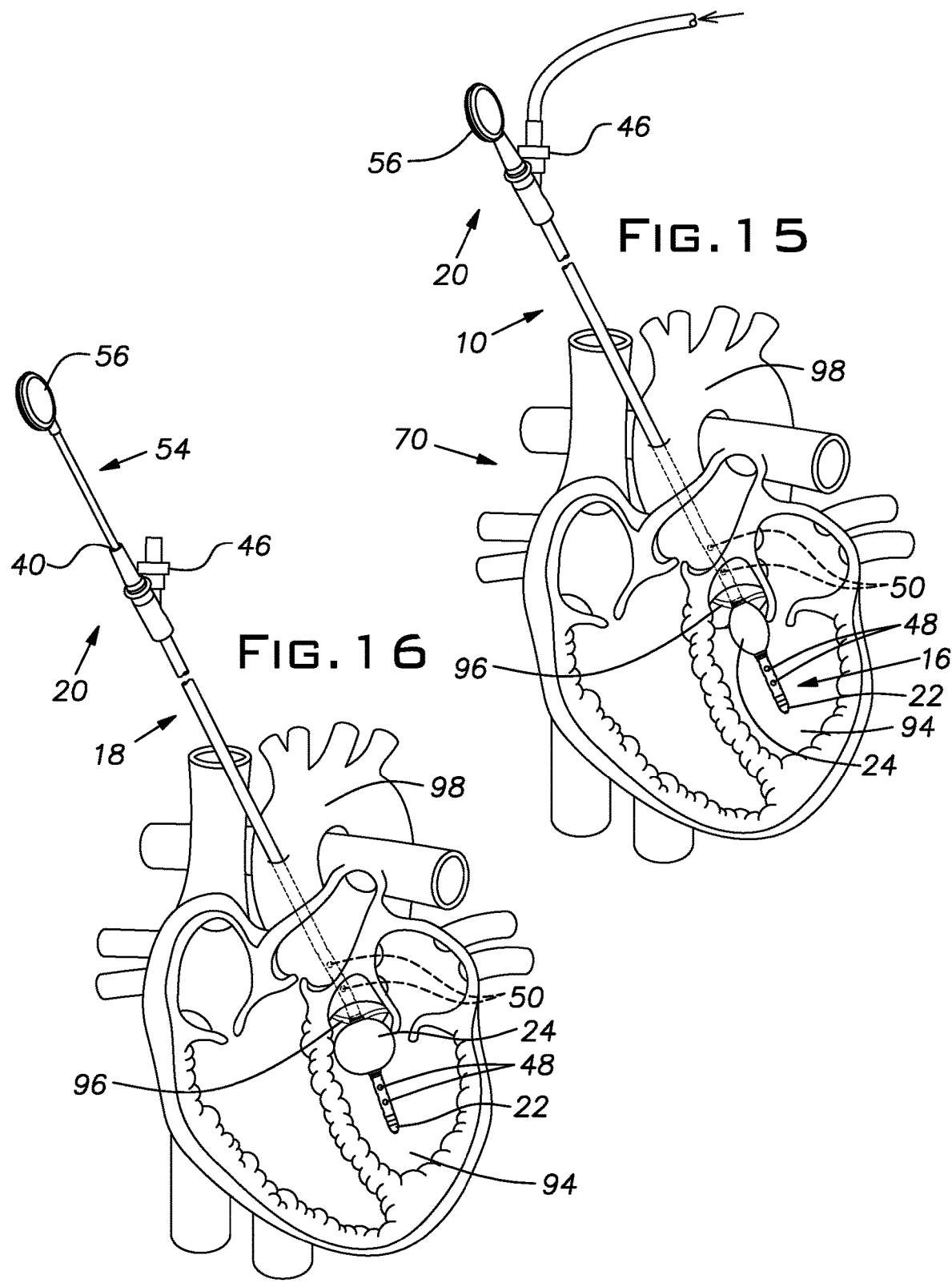

HEART VENT CATHETER AND METHOD OF USE

PRIORITY CLAIM

The present application claims priority from, and incorporates by reference herein for all purposes:

Nonprovisional application Ser. No. 15,729,035, entitled Left Heart Vent Catheter and Method of Use, filed Oct. 10, 2017 by Robert E. Michler and Albert N. Santilli; and Nonprovisional application Ser. No. 15/591,325, entitled Left Heart Vent Catheter and Method of Use, filed May 10, 2017 by Robert E. Michler and Albert N. Santilli, now abandoned; and Nonprovisional application Ser. No. 14/216,214, entitled Left Heart Vent Catheter, filed Mar. 17, 2014 by Robert E. Michler and Albert N. Santilli, now abandoned; and provisional application Ser. No. 61/801,957, entitled Left Heart Vent Catheter, filed Mar. 15, 2013 by Robert E. Michler and Albert N. Santilli.

The present application is a continuation-in-part of the '035 application, which is a continuation-in-part of the '325 and '214 applications. The '325 application was a continuation of the '214 application, which claimed the benefit of the '957 application.

BACKGROUND OF THE INVENTION

Field of the Invention

The present invention relates to heart vent catheters and methods for their use.

Description of the Prior Art

In the course of conducting coronary surgery, it sometimes is necessary to provide a direct or indirect vent of portions of the heart, such as the left ventricle. This is accomplished by inserting an elongate, narrow, hollow tube into the ventricle. The distal end of the tube has a plurality of openings that permit air and blood to enter the tube and be conveyed out of the body.

A commercially known left heart vent catheter is marketed by Medtronic, Inc. of Minneapolis, MN under the trademark DLP. A specification sheet can be found at http://www.medtronic.com/mics/documents/200805572_EN.pdf (page VII-5) and at http://www.medtronic.com/content/dam/medtronic-com-m/mdt/cardio/documents/2011-medtrnc-cannulae-catalog.pdf. The catheter in question and the specification sheet are incorporated herein by reference for all purposes. The catheter in question is provided with a so-called guidewire introducer that maintains the catheter in a desired shape as it is being pushed into place. The guidewire introducer is withdrawn after the distal end of the catheter has been properly positioned, leaving the hollow tube in place to receive and discharge air and blood.

A problem with the catheter in question is that it can shift or otherwise move during the course of a surgical procedure. In particular, the catheter can be withdrawn if care is not taken or it can migrate forward in an unsafe manner, possibly rupturing the heart wall. In order to prevent undesired movement or withdrawal of the catheter, it usually is manually held in place or is sutured in place. Both of these approaches to retaining the catheter in place have a number of drawbacks, such as the need to dedicate a person to carrying out the task or finding a suitable and safe place to suture the catheter to the heart or the additional time it requires to suture the catheter to an appropriate portion of the patient's body.

U.S. Pat. No. 6,117,105 to Bresnaham et al. ("Bresnaham") discloses an aortic catheter and a method for inducing cardioplegic arrest that includes the step of perfusing the patient's aortic arch with fluid through an arch perfusion lumen extending through a catheter shaft. The Bresnaham patent is incorporated herein by reference for all purposes. An objective of Bresnaham is to maintain a perfusion catheter in a precise location within the aorta. Two spaced inflatable members engage the interior walls of the aorta. An upstream occlusion member is designed to block blood flow through the aorta. A downstream anchoring member is designed to hold the catheter shaft in place. Arch perfusion ports and a pressure port are disposed between the upstream occlusion member and the downstream anchoring member.

Bresnaham's device cannot vent portions of the heart. In part, this is because there are no ports or openings in the catheter toward the distal end, i.e., between the forwardmost portion of the upstream occlusion member and the distal end.

In view of the foregoing, there is a need for a heart vent catheter and method of use that can provide a fast, easily operated, effective way to vent desired portions of a patient's heart during surgical procedures. Any such technique preferably would maintain the desired position of the catheter during the course of a surgical procedure without the need to provide a surgical assistant for the purpose of holding the catheter in place or without the need to take the time and trouble to suture the catheter in place.

SUMMARY OF THE INVENTION

The present invention provides a new and improved heart vent catheter and a new and improved technique for holding heart vent catheters in place. In the preferred embodiment, an elongate, flexible tube (hereinafter "tube") defines a first passageway. The tube has a distal (or tip) end, a central portion, and a proximal (or exit) end. The distal end preferably includes a rounded bullet nose or tip at its forwardmost portion. A circumferentially extending, inflatable balloon is included as part of the distal end. The distal end, including the balloon in uninflated condition, and the central portion each have an outer diameter sufficiently small that the tube is capable of extending through a desired portion of the patient's body such as the patient's inferior or superior vena cava or the right pulmonary vein. The distal end, with the balloon uninflated, is capable of extending into a desired portion of the patient's heart such as the left ventricle, right atrium, etc.

The proximal end of the tube includes a vented connector that is in fluid communication with the first passageway. The distal end of the tube is provided with a plurality of openings that establish fluid communication with the first passageway. In the preferred embodiment, openings are disposed on either side of the balloon, i.e., intermediate the forwardmost portion of the balloon and the rounded bullet nose and adjacent the balloon on the side of the balloon opposite the rounded bullet nose. The size, shape, number, and placement of the openings are chosen to permit air, blood, other fluid and preferably at least some debris to pass through the openings and into the first passageway. Desirably, a flow rate of 50 cc per minute or greater can be established under suction applied at the vented connector.

A second passageway extends along at least a portion of the length of the tube. The second passageway establishes fluid communication with the balloon. A branch connector projects from the side of the tube in the region of the proximal end. The branch connector is in fluid communication with the second passageway such that the balloon can be inflated, typically by injecting saline solution by means of a syringe attached to the branch connector.

An elongate stiffening member, or guidewire introducer, can be inserted into, and removed from, the first passageway through the vented connector. The guidewire introducer can be made of a rigid material but more preferably is made of a malleable material such as metal. If desired, a number of visual markers can be provided on the outside of the tube at predetermined locations.

In use, after the guidewire introducer is in place, and if it is made of a malleable material, the tube can be bent into a shape desired by the surgeon. Thereafter, the distal end can be inserted into the heart through an opening formed in the inferior or superior vena cava, the right pulmonary vein, or any other desired location in the heart for application of the device. The extent to which the distal end is inserted into the heart can be gauged by the surgeon through the use of the visual markers.

The distal end can be inserted into a desired part of a patient's heart such as the left ventricle or right atrium. Thereafter, the balloon can be inflated by injecting fluid through the branch connector. The guidewire introducer is removed from the first passageway, preferably after the balloon has been inflated. The inflated balloon will engage a desired part of the patient's heart such as the mitral valve, aortic valve, pulmonary valve or tricuspid valve and thereby prevent undesired withdrawal of the catheter. During the surgical procedure, air, blood, other fluid and debris can be removed from the heart under suction applied through the vented connector. After the surgical procedure has been completed, the balloon can be collapsed by opening the branch connector. After the balloon has been collapsed the catheter can be withdrawn.

The invention eliminates the need to provide a surgical assistant for the purpose of holding the catheter in place, and it avoids the need to take the time and trouble to suture the catheter in place. The invention provides a fast, easily operated, effective way to maintain the desired position of the catheter during the course of a surgical procedure.

BRIEF DESCRIPTION OF THE DRAWINGS

The foregoing and other features and advantages of the present invention will become apparent to those skilled in the art to which the present invention relates upon reading the following description with reference to the accompanying drawings, in which like reference characters refer to like elements through the different figures and in which:

FIG. 1 is a perspective view of a heart vent catheter according to the invention;

FIG. 2 is a top plan view of the heart vent catheter of FIG. 1;

FIG. 3 is a cross-sectional view of the catheter of FIG. 1 taken along a section indicated by line 3-3 in FIG. 2;

FIG. 4 is a cross-sectional view of the catheter of FIG. 1 taken along a section indicated by line 4-4 in FIG. 2;

FIG. 5 is a view of a stiffening member, or guidewire introducer, used with the invention;

FIG. 6 is an enlarged, cross-sectional view of the distal end of the heart vent catheter of FIG. 1 with a retention balloon collapsed;

FIG. 7 is an enlarged, cross-sectional view of the distal end of the heart vent catheter of FIG. 1 with the retention balloon inflated;

FIG. 8 is a schematic representation of a human heart, partly in section, with the catheter of FIG. 1 being inserted into a patient's heart through an opening formed in one of the right pulmonary veins, the catheter having a guidewire introducer extending the length of the catheter;

FIG. 9 is a view similar to FIG. 8, with a distal end portion of the catheter inserted into the left ventricle by passing through the left atrium and the mitral valve;

FIG. 13 is a view similar to FIG. 8, with the catheter being inserted into a patient's heart through an opening formed in the aorta;

FIG. 14 is a view similar to FIG. 13, with a distal end portion of the catheter inserted into the left ventricle by passing through the aortic valve;

FIG. 15 is a view similar to FIG. 14, with a balloon in the process of being inflated to engage the aortic valve;

FIG. 16 is a view similar to FIG. 15, with the guidewire introducer being removed and the balloon fully inflated and engaging the aortic valve.

DESCRIPTION OF THE PREFERRED EMBODIMENT

Figure 10:
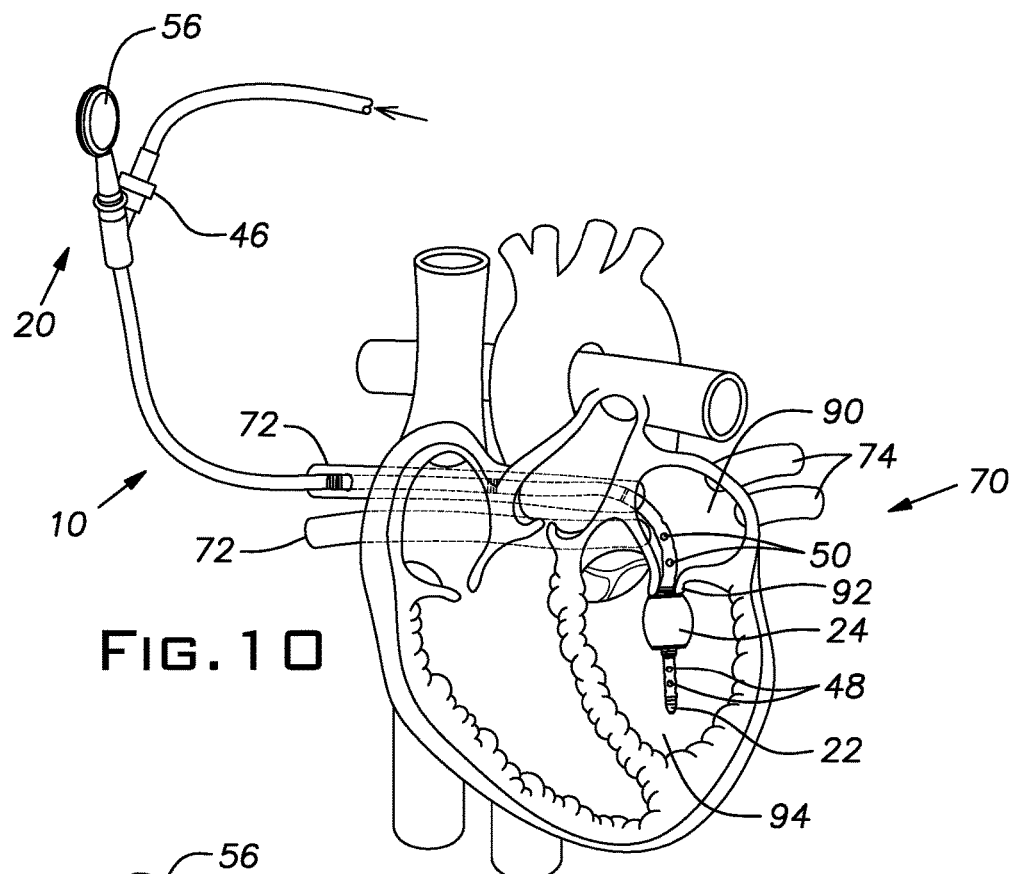
FIG. 10 is a view similar to FIG. 9, with a balloon in the process of being inflated to engage the mitral valve.

Referring now to the drawings, a heart vent catheter according to the invention is indicated by the reference numeral 10. The heart vent catheter 10 includes an elongate, flexible tube 12 made of latex, vinyl, silicone, or similar material that defines a first, hollow passageway 14. The tube 12 has a distal end 16, a central portion 18, and a proximal end 20. The forwardmost portion of the distal end 16 is closed by a generally rounded bullet nose or tip 22.

A thin, circumferentially extending, expansible balloon 24 is included as part of the distal end 16. The balloon 24 is connected to the tube 12 by means of circumferential retainer bands 26. The balloon 24 preferably is made of a high tensile strength silicone rubber such as MED-4027 commercially available from NuSil Technology LLC, Carpinteria, CA 93013. The balloon 24 can accommodate 10 cc of saline solution, and preferably has a maximum capacity of about 15 cc. When inflated with 10 cc of solution (FIG. 4), the balloon 24 assumes the shape of relatively straight end walls 28 connected by an oval center portion 30. When inflated as illustrated, the end walls 28 are spaced from each other approximately 0.95 inch and the outer diameter of the center portion 30 is approximately 1.0 inch.

A second passageway 32 is included as part of a wall 33 that defines the tube 12 (see FIG. 3). Alternatively, the second passageway 32 can be part of a separate tube (not shown) that preferably is disposed within the passageway 14. An opening 34 in the wall 33 provides fluid communication between the second passageway 32 and the interior of the balloon 24.

A formation 36 is connected to the tube 12 and defines a portion of the proximal end 20. The formation 36 includes an end portion 38 having a through opening 40 that communicates with the first passageway 14. The formation 36 also includes a branch tube 42, a check valve 44, and a luer lock connector 46. An opening in the wall 33 provides fluid communication between the second passageway 32 and the interior of the branch tube 42. A small syringe (about 35 ml) (not shown) is adapted to be connected to the branch tube 42 by means of the luer lock connector 46. A syringe, suction line, or drain tube (not shown) can be connected to the end portion 38 in order to drain blood, air or other fluid or debris from the passageway 14 through the opening 40.

A plurality of small openings 48 are formed in the distal end 16, between the tip 22 and the forwardmost end wall 28 of the balloon 24. Preferably 10 openings 48 are provided, each approximately 2.5 mm in diameter. The openings 48 are provided in pairs that open through the tube 12 on opposite sides of the tube 12. Each pair of the openings 48 is oriented approximately 90 degrees relative to adjacent pairs of the openings 48 as measured along a centerline extending through the center of the tube 12. The size, shape and placement of the openings 48 are such that a large quantity of air, blood and debris can flow into the passageway 14 while preventing or minimizing clogging and while maintaining the structural integrity of the tube 12.

A plurality of small openings 50, similar to the openings 48, are formed in the distal end 16. The openings 50 are adjacent to the balloon 24 but on the proximal side thereof. Preferably 10 openings 50 are provided, each approximately 2.5 mm in diameter. The openings 50 extend through the tube 12 and are arranged relative to each other in the same manner as the openings 48. As with the openings 48, the size, shape and placement of the openings 50 permits a large quantity of air, blood and debris to flow into the passageway 14 while preventing or minimizing clogging and while maintaining the structural integrity of the tube 12.

An elongate stiffening member, or guidewire introducer 54 (FIG. 5), can be used to provide stiffness to the tube 12 for purposes of easier and more accurate insertion of the distal end 16 into the patient's heart. The guidewire introducer 54 has a large formation 56 at the proximal end for gripping purposes and a tapered tip 58 at the distal end. The guidewire introducer 54 can be made of a rigid material but more preferably is made of a malleable material such as metal. In order to reduce the force required to insert and remove the guidewire introducer 54 from the first passageway 14, the guidewire introducer 54 may be coated with an anti-friction material such as PTFE.

A number of visual markers 60, 62, 64 are provided for the outside of the tube 12. The markers 60, 62, 64 are evenly spaced at 50 mm±0.51 mm intervals along the length of the central portion 18. The first marker 60 preferably is located 100 mm±2 mm from the tip 22, the second marker 62 preferably is located approximately 150 mm from the tip 22 and the third marker 64 preferably is located approximately 200 mm from the tip 22. The marker 60 consists of a single line, the marker 62 consists of two spaced lines, and the marker 64 consists of three spaced lines. The 100 mm measurement for the first marker 60 is to the edge of the line closest to the tip 22, the 150 mm measurement for the second marker 62 is to a position between the two spaced lines, and the 200 mm measurement for the third marker 64 is to the middle line. The use of one, two and three lines, respectively, for the markers 60, 62, and 64, will inform the surgeon that the markers are located at 100, 150 and 200 mm from the tip 22.

The maximum diameter of the inflated balloon 24 should not exceed 1.0 inch±0.10 inch. The distal side of the balloon 24 should be spaced approximately 1.25 inches from the end of the rounded tip 22. The maximum width of the balloon should be 0.95 inch+0.20 inch/−0.10 inch. The openings 48 should be disposed between the tip 22 and the distal side of the balloon 24, but should be at least 0.8 mm±0.1 mm away from the distal side of the balloon 24. Similarly, the openings 50 should be disposed close to the balloon 24 on the proximal side thereof, but should be at least 0.8 mm±0.1 mm away from the proximal side of the balloon 24.

The length of the combined distal end portion 16 and the central portion 18 is approximately 15.0 inches, while the exit end portion 20 is approximately 2.2 inches long. The tube 12 has an outer diameter of about 0.213 inch and an inner diameter of about 0.105 inch. The second passageway 32 has a diameter of about 0.030 inch.

Because the invention is intended for use in coronary surgery, most of the foregoing dimensions are important or critical and not merely approximations. In particular, the size and shape of the openings 48, 50 and the location of the openings 48, 50 relative to each other and to the balloon 24 and the tip 22 are important to the successful operation of the invention. These openings 48, 50 are large enough to permit not only air and blood to be removed from the heart, but also at least some debris can be removed without clogging the openings 48, 50. The size, shape and placement of the openings 48, 50 permit a flow rate of equal to or greater than 50 cc per minute under suction. This flow rate is believed to be important to the successful operation of the device.

Operation

It is expected that the catheter 10 will be a relatively inexpensive, disposable device suitable for one-time use. The catheter 10 will be provided to the customer in a sterile package with the balloon 24 uninflated. The catheter 10 can be provided to the customer with the guidewire introducer 54 already inserted into the hollow passageway 14, or it can be provided to the customer with the guidewire introducer 54 as a separate component.

In order to use the guidewire introducer 54 with the catheter 10, the tapered tip 58 of the guidewire introducer 54 is inserted into the through opening 40. The entire guidewire introducer 54 then is inserted into the passageway 14 by grasping and pushing the formation 56. After the guidewire introducer 54 is in place, and if it is made of a malleable material, the tube 12 can be bent into a shape desired by the surgeon.

Figure 11:
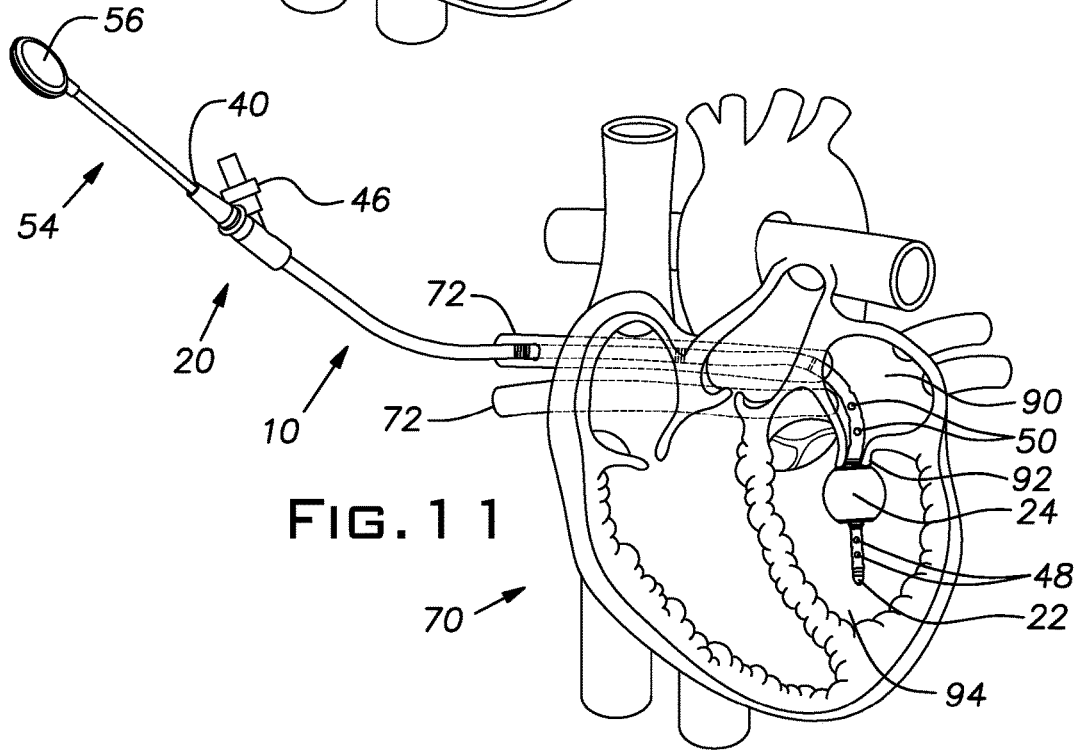
FIG. 11 is a view similar to FIG. 10, with the guidewire introducer being removed and the balloon fully inflated and engaging the mitral valve.
Figure 12:
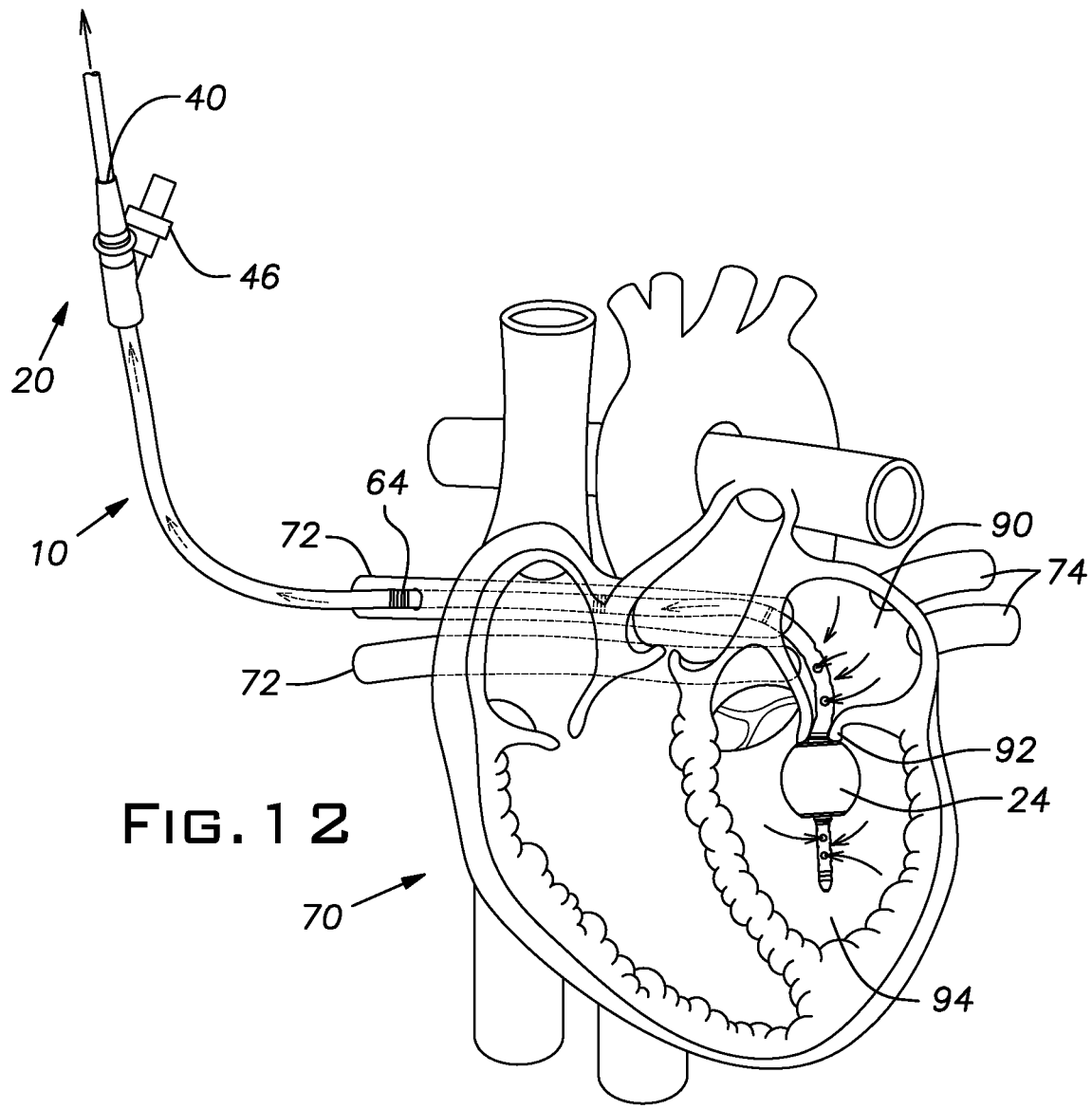
FIG. 12 is a view similar to FIG. 11, with suction being applied to the catheter in order to remove blood, air, and/or debris from the left ventricle.
Figure 17:
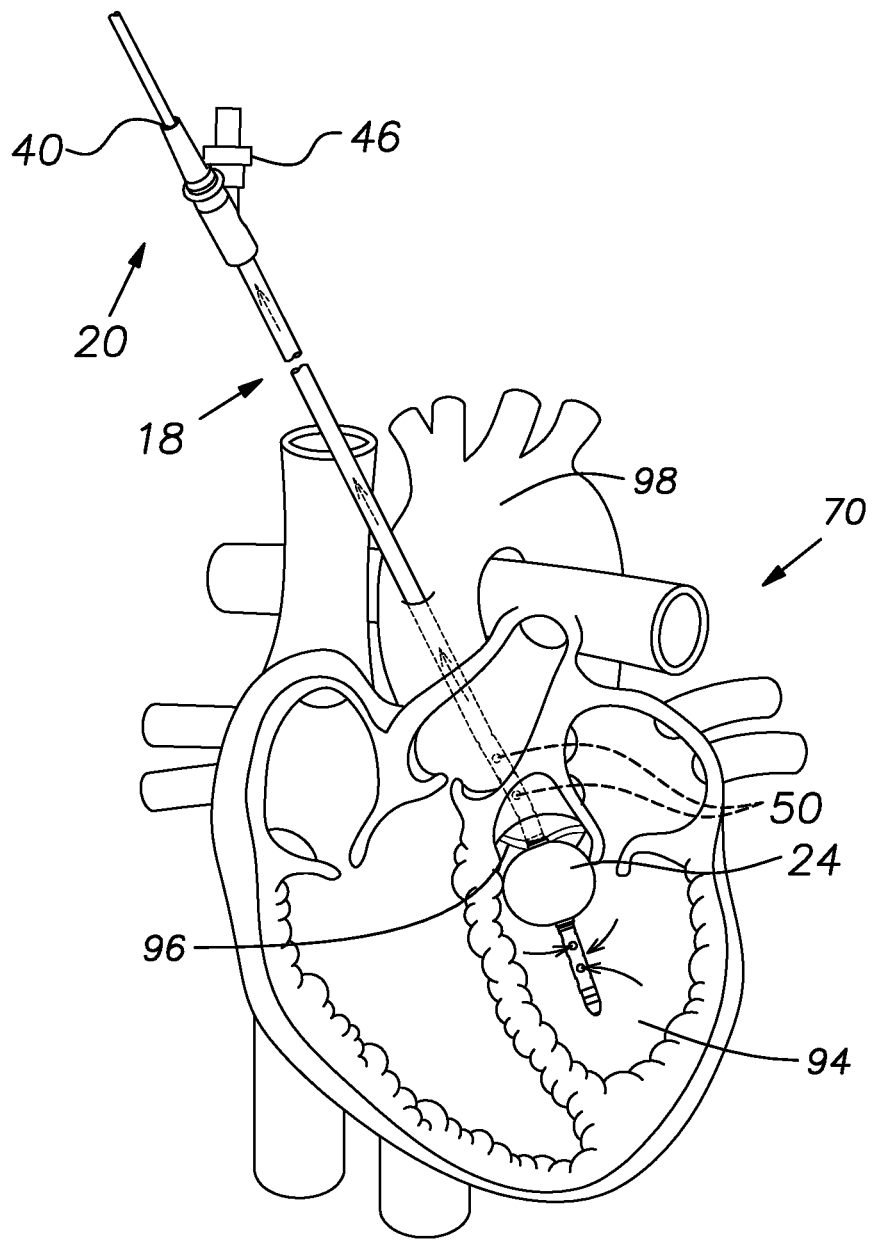
FIG. 17 is a view similar to FIG. 16, with suction being applied to the catheter in order to remove blood, air, and/or debris from the left ventricle.

Referring particularly to FIGS. 8-17, a schematic representation of a human heart 70 is shown. The components are identified by reference numerals, as follows:

72 pulmonary veins (from right lung to left atrium)
74 pulmonary veins (from left lung to left atrium)
76 pulmonary artery (right ventricle/pulmonic valve to right lung)
78 pulmonary artery (right ventricle/pulmonic valve to left lung)
80 pulmonic valve (right ventricle to pulmonary artery)
82 inferior vena cava (lower body to right atrium)
84 superior vena cava (upper body to right atrium)
86 right atrium
87 tricuspid valve
88 right ventricle
90 left atrium
92 mitral valve
94 left ventricle 96 aortic valve
98 aorta (to upper body)
100 aorta (to lower body)

The distal end portion 16 is inserted into the heart 70 through an opening formed in a member such as the inferior or superior vena cava 82, 84, one of the right pulmonary veins 72 or any other desired location in the heart 70 for application of the device. The extent to which the rounded tip 22 is inserted into the heart 70 can be gauged by the surgeon through the use of the markers 60, 62, 64.

In a typical situation (for example, FIGS. 8-12), the distal end portion 16 will be inserted into and through the right superior pulmonary vein 72, across the mitral valve 92, and into the left ventricle 94, or it can be introduced directly into the left ventricle 94 during the course of mitral valve surgery. The soft balloon 24 can be inflated in the left ventricle 94, keeping the tip 22 of the distal end 16 below the mitral valve 92 to enable drainage of blood, air or debris from the left ventricle 94. In addition, the openings 50 on the proximal side of the balloon 24 will enable drainage of blood, air or debris from areas above the mitral valve 92, e.g., the left atrium 90.

After the distal end 16 has been properly positioned, the balloon 24 is inflated with about 10 cc of saline solution by a syringe connected to the branch tube 42. The check valve 44 will retain the saline solution in the catheter so that the syringe can be removed, if desired. In an alternative construction, the check valve 44 can be eliminated. Without a check valve, the syringe must be kept in place for the duration of the surgical procedure in order to retain the saline solution in the balloon 24 and thereby keep the balloon 24 inflated.

Regardless of the manner by which the balloon 24 is inflated, the balloon 24 will bear against the aortic valve 96, tricuspid valve 87, etc., thereby preventing the catheter 10 from being withdrawn from the heart 70 during the course of the surgical procedure. While the distal end portion 16 is in the heart 70, debris or blood, air or other fluid can be drained or withdrawn under vacuum through the openings 48, 50 and the hollow passageway 14. After there is no need for the catheter 10, the check valve 44 can be opened and/or the syringe removed in order to drain fluid from the balloon 24. This will cause the balloon 24 to be collapsed so as to permit the catheter 10 to be withdrawn from the heart 70.

By using the catheter 10 according to the invention, there no longer is a need to provide a surgical assistant for the purpose of holding a catheter in place. The invention also avoids the need to take the time and trouble to suture a catheter in place. The invention provides a fast, easily operated, effective way to maintain the desired position of the catheter 10 during the course of a surgical procedure. The particular size, shape, and placement of the openings in the distal end of the tip ensure that blood, air, and at least some debris can be removed effectively from the heart under suction without clogging the openings.

Although the invention has been described in detail with reference to particular examples and embodiments, the examples and embodiments contained herein are merely illustrative and are not an exhaustive list. Variations and modifications of the present invention will readily occur to those skilled in the art. The present invention includes all such modifications and equivalents.

What is claimed is:

1. A method of venting desired portions of a patient's heart, including the left or right ventricle or the left or right atrium, comprising:
providing a catheter having:
an elongate, flexible tube that defines a first passageway, the tube having a distal end, a central portion, and a proximal end, the tube being made of a material selected from the group consisting of latex, vinyl, and silicone;
a generally rounded tip included as part of the distal end that defines the forwardmost end of the tube;
a single inflatable balloon included as part of the distal end and surrounding at least a portion of the tube, the balloon when inflated being smooth-sided and capable of engaging the patient's mitral valve, aortic valve, pulmonary valve or tricuspid valve and preventing retraction of the distal end from the left ventricle, right atrium or other desired location in the heart;
wherein the balloon when inflated is defined by a pair of end walls that are spaced from each other approximately 0.95 inch and an oval center portion that has a diameter of approximately 1.0 inch;
a plurality of first openings in the distal end that establish fluid communication with the first passageway, the first openings being disposed between the generally rounded tip and that portion of the balloon closest to the generally rounded tip;
a plurality of second openings in the distal end that establish fluid communication with the first passageway, the second openings being disposed adjacent the balloon on the proximal side thereof;
wherein 10 first openings and 10 second openings are provided in the distal end, each opening being approximately 2.5 mm in diameter, the first and second openings being provided in pairs that open through the tube on opposite sides of the tube, each pair of the first and second openings being oriented approximately 90 degrees relative to adjacent pairs of the first and second openings as measured along a centerline extending through the center of the tube;
the size, shape, and number of first and second openings being such that 50 cc per minute or more of air, blood, other fluid or debris can be withdrawn through the tube under suction;
wherein the step of providing a catheter includes the step of providing circumferentially extending retainer bands that engage each side of the balloon and hold it to the tube, the retainer bands being spaced from the first and second openings closest to the balloon by approximately 0.030 inch;
the distal end with the balloon collapsed and the central portion each having an outer diameter, the outer diameter of the distal end and the central portion being such that they are capable of being fed through the patient's inferior or superior vena cava, the right pulmonary vein or any desired location in the heart for the application of the device and the distal end is capable of extending into the patient's left ventricle, right atrium or other desired location in the heart;
a second passageway that extends along at least a portion of the length of the tube, the second passageway being in fluid communication with the balloon, the tube including a wall and the second passageway is formed as part of the wall;
a branch tube included as part of the proximal end, the branch tube projecting from the side of the elongate, flexible tube, the branch tube being in fluid communication with the second passageway; and a plurality of visual markers disposed on the outside of the tube, the markers being evenly spaced at predetermined intervals along the length of the tube;

providing an elongate stiffening member of a size and shape that permits it to be inserted into and removed from the first passageway;

inserting the elongate stiffening member in the first passageway;

inserting the distal end into a desired portion of the patient's heart by passing the elongate tube through the patient's inferior or superior vena cava, the right pulmonary vein or any desired location in the heart for the application of the device;

removing the elongate stiffening member from the first passageway after the distal end has been inserted into a desired portion of the patient's heart;

inflating the balloon by pumping fluid into the second passageway through the branch tube until the balloon reaches a size to engage the mitral valve, aortic valve, pulmonary valve or the tricuspid valve so as to prevent retraction of the distal end from the desired portion of the patient's heart; and removing blood, other fluid, debris and/or air from the desired portion of the patient's heart by withdrawing the blood, other fluid, debris and/or air through the first openings in the distal end and the first passageway.

2. The method of claim 1, wherein the step of providing a catheter includes providing the plurality of visual markers evenly spaced at 50 mm intervals along the length of the tube, the first marker being located 100 mm from the generally rounded tip.

3. The method of claim 1, wherein the step of providing a catheter includes providing three visual markers, the first marker consisting of a single circumferentially extending line, the second marker consisting of two closely spaced circumferentially extending lines, and the third marker consisting of three closely spaced circumferentially extending lines.

4. The method of claim 1, wherein the step of removing blood, other fluid, debris and/or air from the desired portion of the patient's heart by withdrawing the blood, other fluid, debris and/or air through the first openings in the distal end and the first passageway is accomplished by applying a vacuum to the first openings in the distal end and the first passageway.

* * * * *